United States Patent
Zhang et al.

(10) Patent No.: US 12,357,766 B2
(45) Date of Patent: Jul. 15, 2025

(54) SAFE INSULIN NEEDLE

(71) Applicant: BERPU MEDICAL TECHNOLOGY CO., LTD., Wenzhou (CN)

(72) Inventors: Hongjie Zhang, Wenzhou (CN); Xingguo Wang, Wenzhou (CN)

(73) Assignee: BERPU MEDICAL TECHNOLOGY CO., LTD., Wenzhou (CN)

( * ) Notice: Subject to any disclaimer, the term of this patent is extended or adjusted under 35 U.S.C. 154(b) by 924 days.

(21) Appl. No.: 17/430,911

(22) PCT Filed: Jan. 21, 2020

(86) PCT No.: PCT/CN2020/073525
§ 371 (c)(1),
(2) Date: Aug. 13, 2021

(87) PCT Pub. No.: WO2020/164382
PCT Pub. Date: Aug. 20, 2020

(65) Prior Publication Data
US 2022/0080130 A1   Mar. 17, 2022

(30) Foreign Application Priority Data

Feb. 15, 2019  (CN) .......................... 201910117472.8

(51) Int. Cl.
  *A61M 5/32*  (2006.01)
  *A61M 5/34*  (2006.01)
  *A61M 5/31*  (2006.01)

(52) U.S. Cl.
  CPC .......... *A61M 5/3202* (2013.01); *A61M 5/346* (2013.01); *A61M 5/348* (2013.01); *A61M 2005/3104* (2013.01)

(58) Field of Classification Search
  CPC .... A61M 5/3202; A61M 5/346; A61M 5/348; A61M 2005/3104; A61M 2005/3247;
(Continued)

(56) References Cited

U.S. PATENT DOCUMENTS

| 5,944,700 A | * | 8/1999 | Nguyen ................. A61M 5/46 604/117 |
| 2011/0071492 A1 | | 3/2011 | Horvath et al. |
| 2018/0028764 A1 | * | 2/2018 | Park ..................... A61M 5/326 |

FOREIGN PATENT DOCUMENTS

| CN | 108371738 A | 8/2018 |
| CN | 108404257 A | 8/2018 |

(Continued)

OTHER PUBLICATIONS

ISR for International Application PCT/CN2020/073525 issued Mar. 31, 2020 and an English Translation.
(Continued)

*Primary Examiner* — Bhisma Mehta
*Assistant Examiner* — Fatimata Sahra Diop
(74) *Attorney, Agent, or Firm* — Ladas & Parry LLP

(57) ABSTRACT

Safe insulin needle assembly includes protection sheath, needle, safety protection sleeve, pressure seat and needle holder. The needle is arranged on the central axis of the needle holder. The pressure seat is sheathed over the upper portion of the needle holder. The safety protection sleeve is sheathed on the needle holder and the pressure seat as a whole. The upper protection of the safety protection sleeve is connected to and cooperates with the pressure seat. The needle protrudes out of the top end of the upper portion of the safety protection sleeve. The lower portion of the safety protection sleeve is connected to and cooperates with the lower portion of the needle holder. The protection sheath is sheathed on the safety protection sleeve and the needle as a whole. The lower portion of the protection sheath is connected to and cooperates with the lower portion of the safety protection sleeve.

7 Claims, 13 Drawing Sheets

(58) Field of Classification Search
CPC .............. A61M 5/3213; A61M 5/3243; A61M 5/3275; A61M 5/3293
See application file for complete search history.

(56) References Cited

FOREIGN PATENT DOCUMENTS

| | | |
|---|---|---|
| CN | 109316650 A | 2/2019 |
| CN | 109718429 A | 5/2019 |
| CN | 209996935 U | 1/2020 |

OTHER PUBLICATIONS

Written Opinion for International Application PCT/CN2020/073525 mailed Apr. 20, 2020.

* cited by examiner

4

4

SAFE INSULIN NEEDLE

CROSS REFERENCE TO RELATED APPLICATIONS

This application is a national stage entry of International Patent Application No. PCT/CN2020/073525, filed on Jan. 21, 2020, which claims priority to Chinese Patent Application No. 201910117472.8, filed on Feb. 15, 2019. The aforementioned patent applications are hereby incorporated by reference in their entirety.

TECHNICAL FIELD

The present invention relates to the field of injection syringe, in particular a safe insulin needle assembly.

BACKGROUND ART

A safe insulin needle assembly is disclosed in the document 1 of which the application number is CN201810117903.6, the application date is Feb. 6, 2018, the publication number is CN108404257A, the publication date is Aug. 17, 2018, and the applicant is Berpu Medical Technology Co. Ltd.

The safe insulin needle assembly includes a needle, a safety protection sleeve and a needle holder, wherein the needle holder is provided on the central axis thereof with the needle distributed along the central axis, and is provided on the lower part with a matching cavity into which the lower end of the needle extends, and is provided on the upper part with a mounting seat the upper part of which the upper end of the needle extends into upward, is provided over the outer part thereof with a safety protection sleeve having the inner wall within its cavity to engage with the outside wall of the needle holder in a locking manner. The safety protection sleeve is formed by the upper part and the lower part and has a tubular hollow cavity, is provided on the lower part thereof and on the inner wall of the cavity thereof with at least one location vertical bar the lower end of which biases toward one side so as to form a position-limiting step which is distributed in the form of protrusion on the inner wall of the cavity of the under part of the safety protection sleeve. The safety protection sleeve is provided on the upper part thereof and the inner wall of the cavity thereof with a position-limiting protruding bar having a protruding point and provided on the lower end side with a flat plane and orienting along and parallel to the axis of the safety protection sleeve. The safety protection sleeve is provided on the inner wall thereof and on the cavity thereof with an annular position-limiting ring which is set in the manner of protrusion on the inner wall of the cavity. The safety protection sleeve is provided on the top end of the upper part thereof with a needle penetration hole.

The matching cavity is provided on the outside wall thereof with at least one position-limiting bar distributed in a manner of protrusion on the outside wall of the matching cavity and cooperating with above-mentioned location vertical bar. The lower end of the position-limiting bar forms a position-limiting plane to cooperating with the above-mentioned position-limiting step.

The needle mounting seat is provided on the outside wall thereof with a slide to cooperate with the position-limiting protrusion bar and provided on the surface thereof with a lower protrusion point and an upper protrusion point distributed respectfully upward and downward. The slide is provided on one side of the upper end thereof with a transitional angled plane in the convex form, one side of which forms a locking area of which one side forms prevention block in the convex form. The locking area is placed between the transitional angled plane and the prevention block. The transitional angled plane is provided on the inward side thereof with an anti-reversal platform. The anti-reversal platform on each side of the locking area is flat and the inner wall of the prevention block is also flat. The inner wall on each side is used for position limiting the position-limiting protrusion bar. The lower end of the locking area forms a position-limiting platform used to cooperate with the plane of the lower end of the above-mentioned position-limiting protrusion bar. The slide and the locking area are distributed alternately on the outside wall of the needle mounting seat. A locking area is placed between the adjacent slides. The locking area is provided on the lower edge thereof with position-limiting block protruding from the outside wall of the needle mounting seat to cooperate with the above-mentioned position-limiting ring so as to prevent the position-limiting ring from upward movement.

In the insulin needle assembly, the structure between the upper part of the needle holder and the upper part of the safety protection sleeve is not stable and the safety protection sleeve after self-locking remains a risk of being unlocked and hence needs to be reconceived.

SUMMARY OF THE INVENTION

In order to solve the above-mentioned defects in the prior art, the present invention aims to provide a safe insulin needle assembly.

The aim of the invention will be realized by the following solution:

A safe insulin needle assembly characterized in that comprising a protection sheath, a needle, a safety protection sleeve, a pressure seat and a needle holder, the needle is arranged on the central axis of the needle holder, the pressure seat is sheathed over the upper portion of the needle holder; the safety protection sleeve is sheathed on the needle holder and the pressure seat as a whole; the upper portion of the safety protection sleeve is connected to and cooperates with the pressure seat; the needle protrudes out of the top end of the upper portion of the safety protection sleeve; the lower portion of the safety protection sleeve is connected to and cooperates with the lower portion of the needle holder; the protection sheath is sheathed on the safety protection sleeve and the needle as a whole; and the lower portion of the protection sheath is connected to and cooperates with the lower portion of the safety protection sleeve;

the protection sheath having a hollow cavity; an upper portion in the form of hollow truncated cone; a lower portion in the form of cylinder, the diameter of the lower portion is larger than that of the lower edge of the upper portion of the protection sheath; a first location step in an annular form, provided at the connection between the upper portion and the lower portion of the protection sheath; a top end in a closed form, on the upper portion of the protection sheath; an inner wall on the lower portion of the protection sheath, provided thereon with at least two first inner circular vertical bar uniformly distributed along the circumference, oriented in the axial direction;

the safety protection sleeve having a hollow cavity; an upper portion and a lower portion each in the form of cylinder; an top end on the upper portion, provided thereon with needle penetration hole, the diameter of the upper portion being smaller than that of the lower portion; a second location step, in an annular form, provided at the connection between the upper portion and the lower portion; the first location step cooperating with the second location step in the manner of axial position limiting; the outer wall on the lower portion of the safety protection sleeve provided thereon with a circular outer location protrusion boss along the lower edge of the outer wall, with at least two outer location bars uniformly distributed along the circumference, oriented in the axial direction and having a lower end which is linked to the outer location protrusion boss; a free position surface provided between the outer location bars, used for the insertion of the first inner circular vertical bar and interference fit therebetween;

an inner wall on the upper portion of the safety protection sleeve, provided thereon with at least two second inner circular vertical bars uniformly distributed along the circumference and at least one first location vertical bar, each oriented in the axial direction; the first location vertical bar provided thereon with a protrusion point, having a lower end provided thereon with a position-limiting protrusion protruded to each side; the inner wall of the upper portion of the safety protection sleeve provided thereon with a circular inner position-limiting protrusion boss along the lower edge of the inner wall; an inner wall on the lower portion of the safety protection sleeve provided thereon with at least two third inner circular vertical bars uniformly distributed along the circumference and at least one second location vertical bar, each oriented in the axial direction; a lower end on the second location vertical bar and being provided thereon with a position-limiting step protrusion deflected to one side;

the pressure seat being in a cylinder form, having an outer wall provided on the upper edge thereof with at least two position-limiting protrusion bosses uniformly distributed along the circumference, the position-limiting protrusion boss having an outer side snugly fitting the inner wall of the upper portion of the safety protection sleeve, the position-limiting protrusion boss cooperating with the inner position-limiting protrusion boss of the safety protection sleeve in a manner of axial position limiting, a position-limiting opening provided between two adjacent position-limiting protrusion bosses, used for upward penetration of the second inner circular vertical bar and first location vertical bar of the safety protection sleeve; the position-limiting protrusion bosses each having a upper surface provided thereon with a position-limiting block, the part between two adjacent position-limiting blocks constituting an anti-reversal tooth groove, the position-limiting block and the anti-reversal tooth groove cooperating with the position-limiting protrusion on the lower portion of the first location vertical bar of the safety protection sleeve; the outer wall of the pressure seat provided thereon with at least two outer guidance flanges uniformly distributed along the circumference, corresponding to the position limiting protrusion bosses respectively, oriented in the axial direction and cooperating with the second inner circular vertical bar and the first location vertical bar of the safety protection sleeve; the outer guidance flange having an upper end, between the upper ends on two adjacent outer guidance flanges being provided thereon with protrusion flange along the circumference, interference fitting the protrusion point on the first location vertical bar of the safety protection sleeve; the inner wall of the pressure seat having a middle portion which is provided thereon with at least two clutch protrusions uniformly distributed along the circumference, the inner wall of the pressure seat having a lower portion which is provided thereon with at least two inner guidance flanges uniformly distributed along the circumference, oriented in the axial direction;

the needle holder having an upper portion in a tube form, an outer wall on the upper portion provided thereon with at least two guidance fastening flanges uniformly distributed along the circumference, oriented in the axial direction and cooperating with the inner guidance flange of the pressure seat, the guidance fastening flange provided thereon with a clutch opening cooperating with the clutch protrusion of the pressure seat; the needle holder having a lower portion in a cylindrical form, the lower portion having an upper end face cooperating with the second location step of the safety protection sleeve in a manner of axial position limiting, the lower portion of the needle holder having an outer wall provided thereon with at least two position-limiting vertical bar and at least one position-limiting bar uniformly distributed along the circumference, each oriented in the axial direction and cooperating with the third inner circular vertical bar and second location vertical bar of the safety protection sleeve, the position-limiting bar having a lower end cooperating with the position-limiting step protrusion on one side of the lower end of the second location vertical bar of the safety protection sleeve; the lower portion on the needle holder having an inner cavity which is provided thereon with a radial platform having an upper side linked to the upper portion of the needle holder, the radial platform cooperating with the inner position-limiting protrusion boss of the safety protection sleeve and the lower end face of the pressure seat in a manner of axial position limiting, the inner wall on the lower portion of the needle holder having a part corresponding to the lower portion of the radial platform, which is provided with thread.

Preferably, at least one of the lower end on the first inner circular vertical bar of the protection sheath, the top end on the outer location bar of the safety protection sleeve, the top end on the first location vertical bar of the safety protection sleeve and the top end on the guidance fastening flange is shaped as a triangular head.

Preferably, the inner position-limiting protrusion boss is linked to the lower end of the second inner circular vertical bar, is provided on the part corresponding to the lower end of the first location vertical bar with a gap.

Preferably, the upper end on the outer guidance flange of the pressure seat is linked to the corresponding position-limiting protrusion boss.

Preferably, the lower ends of the two adjacent position-limiting vertical bars of the needle holder is provided therebetween with position-limiting platform along the circumference, cooperating with the lower end on the third inner circular vertical bar of the safety protection sleeve so that the axial downward movement of the safety protection sleeve is prevented.

Preferably, the lower end of the position-limiting bar is flat in such a manner that the lower end cooperates with the plane on the position-limiting step protrusion on one side of the lower end on the second location vertical bar of the safety protection sleeve.

Preferably, the needle is secured on the upper portion of the needle holder with the upper end upward penetrating out of the top end on the upper portion of the needle holder and out of the needle penetration hole of the safety protection sleeve, the lower end of the needle downward penetrating through the radial platform and extending into the inner cavity of the lower portion of the needle holder.

DESCRIPTION OF REFERENCE NUMERALS IN THE DRAWINGS

1 protection sheath;
101 first location step;
102 first inner circular vertical bar;
2 needle;
3 safety protection sleeve;
301 needle penetration hole;
302 second location step;
303 outer location convex boss;
304 outer location bar;
305 free positioning surface;
306 second inner circular vertical bar;
307 first location vertical bar;
308 convex point;
309 position limiting protrusion;
310 inner position-limiting boss;
311 gap;
312 third inner circular vertical bar;
313 second location vertical bar;
314 position-limiting step protrusion;
4 pressure seat;
401 position-limiting boss;
402 position-limiting opening;
403 position-limiting block;
404 anti-reversal tooth groove;
405 outer guiding flange;
406 convex flange;
407 fastening protrusion;
408 inner guiding flange;
409 guiding groove;
5 needle holder;
501 guiding fastening flange;
502 clutch opening;
503 position-limiting vertical bar;
504 position-limiting bar;
505 position-limiting boss;
506 radial platform;
507 inside screw;
6 insulin pen.

DETAILED DESCRIPTION

Hereinafter, the specific embodiment of the present invention is illustrated in combination of the drawings in such a way that those skilled in the art will more clearly understand how the present invention is realized. Although the best embodiments illustrated as below teaches the present invention, they are only to show the substance of the invention by the examples, not to limit the scope of protection of the present invention.

Figure 1:
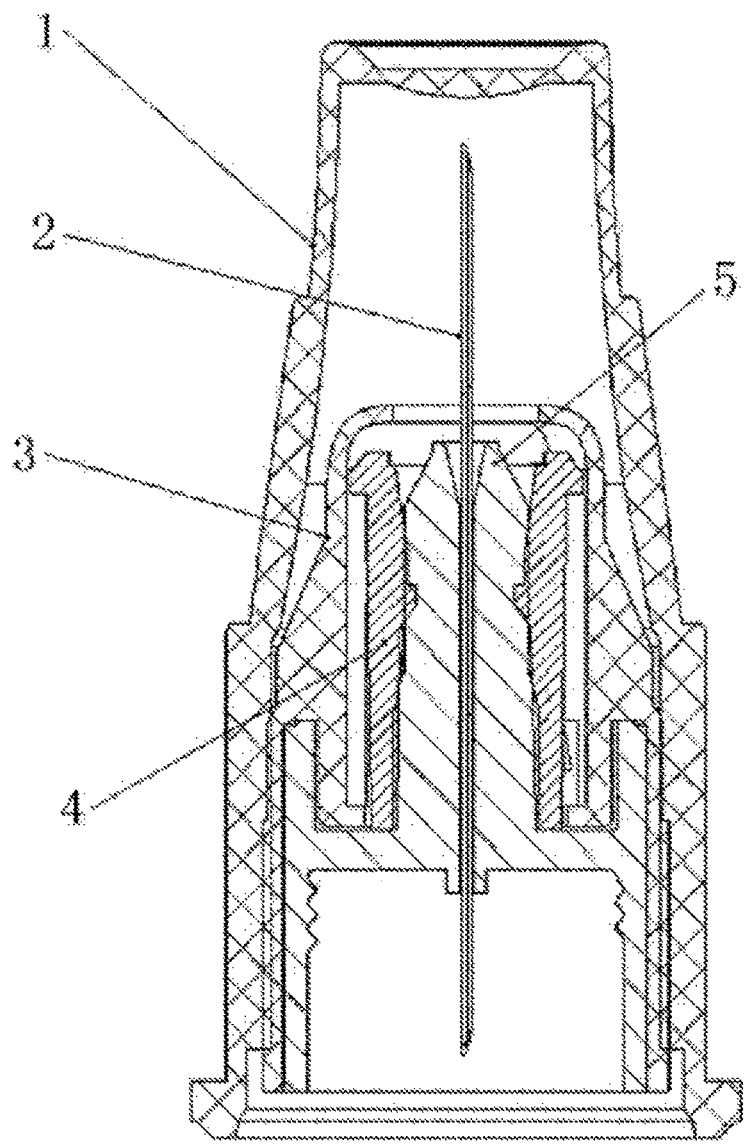
FIG. 1 is a cut view of the present invention.
Figure 2:
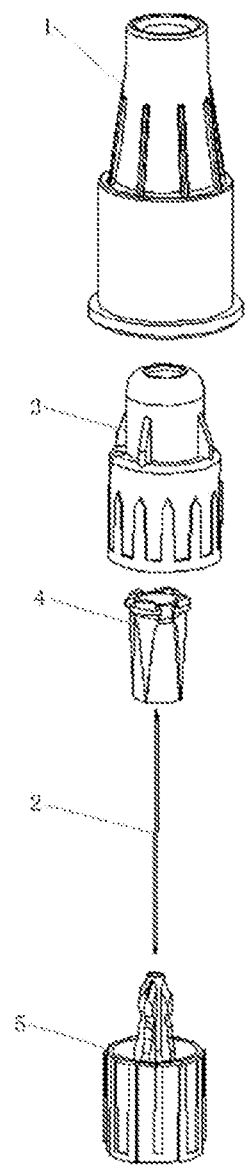
FIG. 2 is an exploded illustrative view of the present invention.

As seen in FIG. 1 and FIG. 2, a safe insulin needle assembly, comprises a protection sheath 1, a needle 2, a safety protection sleeve 3, a pressure seat 4 and a needle holder 5. The needle holder 5 is provided on the central axis thereof with the needle 2, over the upper part thereof with the pressure seat 4. The needle holder 5 and the pressure seat are integrally covered with the safety protection sleeve 3 the upper part of which cooperates and coupled with the pressure seat. The needle 2 penetrates the top side of the safety protection sleeve 3 whose lower part cooperates and is coupled with the lower part of the needle holder 5. The protection sheath 1 fits over the whole of the safety protection sleeve 3 and the needle 2. The lower part of the protection sheath 1 cooperates and is coupled with the lower part of the safety protection sleeve 3.

Figure 3:
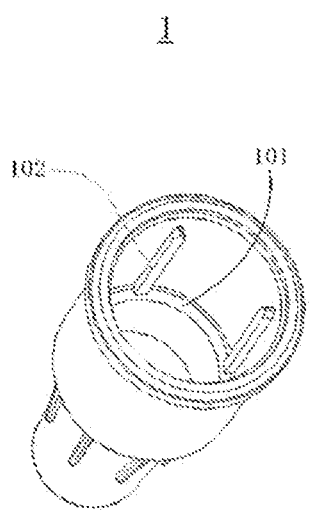
FIG. 3 is a structural schematic view of the protection sheath of the present invention.

As illustrated in FIG. 3, the protection sheath 1 is hollow and has an upper part in the form of hollow truncated cone, which mainly covers the needle 2 and protects the needle when the needle is not used, the protection sheath 1 has a lower part in the form of cylinder. The diameter of the lower part of the protection sheath 1 is larger than that of the lower edge of the upper part of the protection sheath 1 in such a manner that the connection position between the upper part and the lower part of the protection sheath 1 is shaped as a first location step 101 in an annular form. The top side of the upper part of the protection sheath 1 is closed. The protection sheath 1 is provided on the inner wall of the upper part thereof with at least two first inner circular vertical bars 102 distributed evenly along the circumference, which is oriented axially and has a lower end in the form of triangular head for guidance.

Figure 4:
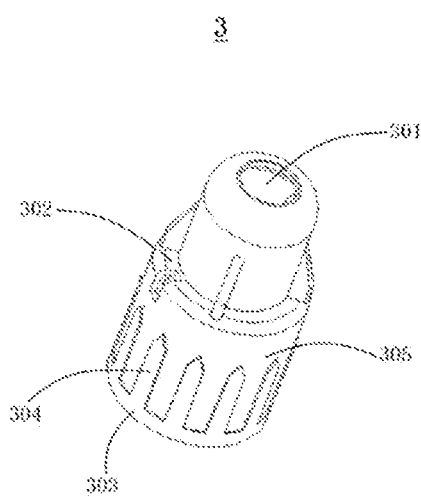
FIG. 4 is a structural schematic view of the safety protection sleeve of the present invention.

As illustrated in FIG. 4, the protection sleeve 3 has a hollow cavity, an upper part provided on the top end thereof with a needle penetration hole 301 coaxial with the protection sleeve, and a lower part in the form of cylinder. The diameter of the upper part of the safety protection sleeve 3 is smaller than that of the lower part of the safety protection sleeve 3 in such a manner that connection position between the upper part and lower part of the safety protection sleeve 3 is shaped as a second location step 302 in an annular form, to cooperate with the first location step 101 in a manner of limiting axial position, and to abut upward onto the first location step 101 so as to prevent the safety sleeve 3 from further upward movement into the upper part of the protection sheath 1. The safety protection sleeve 3 is provided on the outside wall of the lower part thereof with a circular outer location protrusion boss 303 along the lower edge thereof, and is provided on the outside wall of the lower part thereof with at least two outer location bars 304 evenly distributed along the circumference thereof, which is placed axially and has a lower end coupled to the outer location boss 303 and has an upper end in triangular head. The safety protection sleeve 3 is provided on the rest part of the outside wall of the lower part thereof with a free position surface 305. Those free position surfaces 305 between at least two outer location bars 304 are used for insertion of the first inner circular vertical bars 102 of the said protection sheath 1 and for interference fit with the first inner circular vertical bar 102 so as to prevent the safety protection sleeve 3 and the protection sheath 1 from rotation in relation to each other and hence to keep them axial movement in relation to each other.

Figure 5:
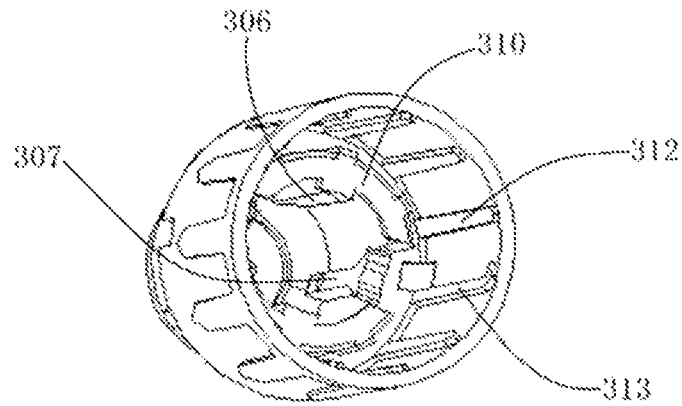
FIG. 5 is another structural schematic view of the safety protection sleeve of the present invention.
Figure 6:
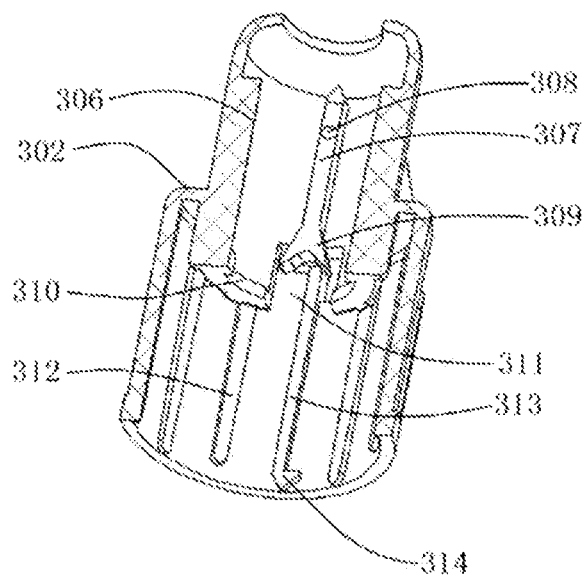
FIG. 6 is a cut view of the perspective structure of the safety protection sleeve of the present invention.

As illustrated in FIG. 5 and FIG. 6, the safety protection sleeve 3 is provided on the inner wall of the upper part thereof with at least second inner circular vertical bars 306 uniformly distributed along the circumference and at least one first location vertical bar 307. The second inner circular vertical bars 306 and the first location vertical bar 307 each are oriented along the axial direction. The first location vertical bar 307 is provided thereon with a protrusion point 308 and has an upper end in the form of triangular head, is provided on the lower end thereof with position-limiting protrusion 309 protruded towards each side. The safety protection sleeve 3 is provided on the inner wall of the upper part thereof with a lower edge which extends downward beyond the position the second location step 302 is set, along the lower edge is placed a circular inner position-limiting protrusion boss 310 which is connected with the lower end of the second inner circular vertical bar 306 and is provided on the part corresponding to the lower end of the first location vertical bar 307 with a gap 311. The safety protection sleeve 3 is provided on the inner wall of the lower part thereof with at least two third inner circular vertical bar 312 and at least one second location vertical bar 313 uniformly distributed along the circumference and respectively oriented axially. The second location vertical bar 313 is provided on the lower end thereof with a position-limiting step-like protrusion 314 deflected to one side.

Figure 7:
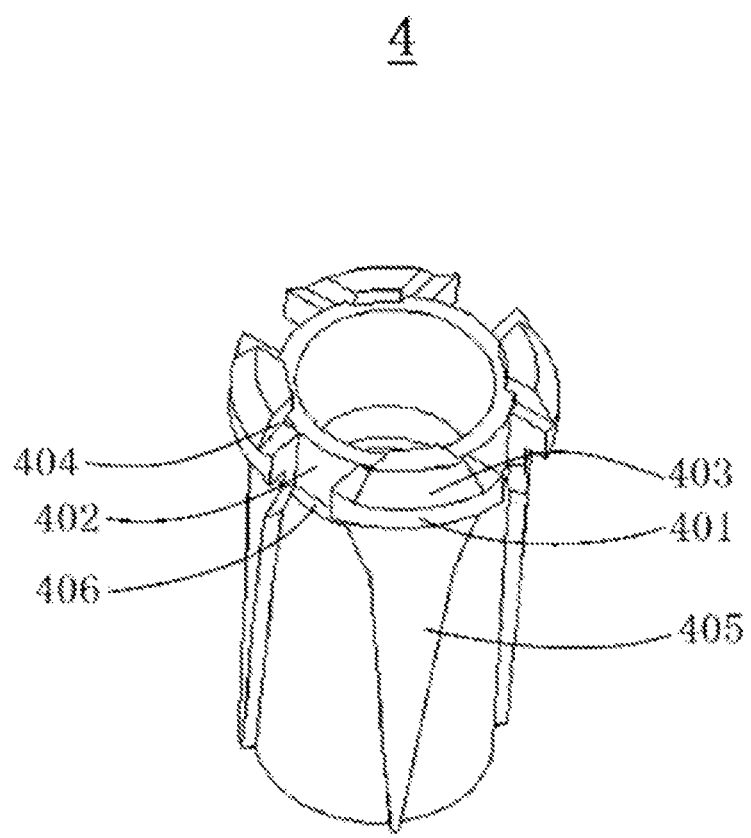
FIG. 7 is a structural schematic view of the pressure seat of the present invention.
Figure 8:
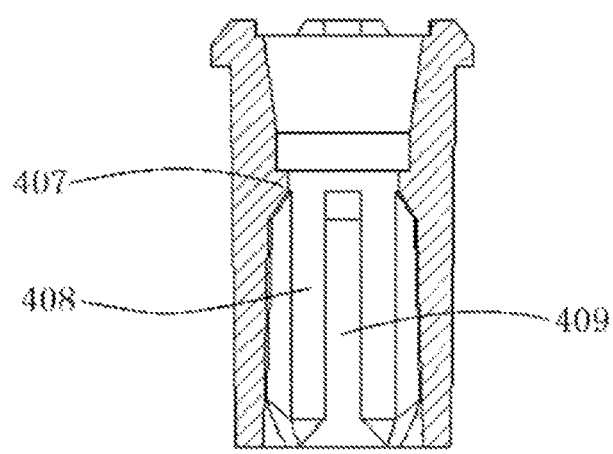
FIG. 8 is a cut view of the pressure seat of the present invention.
Figure 9:
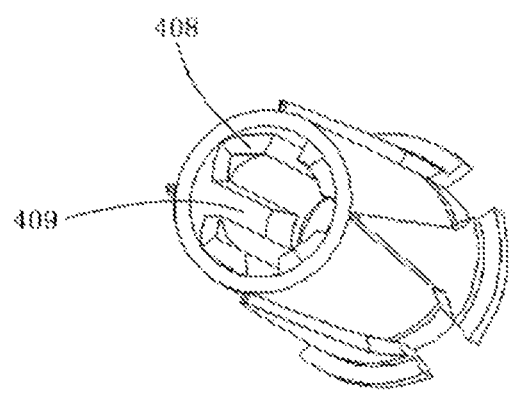
FIG. 9 is another structural schematic view of the pressure seat of the present invention.

As illustrated in FIGS. 7-9, the pressure seat is in a cylindrical form and is provided on the upper edge of the outer wall thereof with at least two position-limiting protrusion bosses 401 uniformly distributed along the circumference, each having an outer side snugly fitting the inner wall of the upper part of the safety protection sleeve 3. The position-limiting protrusion boss 401 cooperates with the inner position-limiting protrusion boss 310 of the safety protection sleeve 3 in a manner of axial position limiting. A position-limiting opening 402 is formed between the adjacent position-limiting protrusion bosses 401 and is used for upward insertion of the second inner circular vertical bar 306 and the first location vertical bar 307 of the safety protection sleeve 3 and for preventing the safety protection sleeve 3 from large range of oscillation in the axial plane. Each of the position-limiting protrusion boss 401 is provided on the upper surface with position-limiting block 403. An anti-reversal tooth groove is formed between the two adjacent position-limiting blocks 403. The position-limiting block 403 and the anti-reversal tooth groove 404 cooperates with the position-limiting protrusion 309 protruded to each side and of the lower end of the first location vertical bar 307 of the safety protection sleeve 3 so as to prevent the first location vertical bar 307 from the movement in the circumference and axial direction. The pressure seat is provided on the outer wall thereof with at least two outer guidance flanges 405 uniformly distributed along the circumference, and is placed corresponding to the position-limiting protrusion boss 401. The outer guidance flange 405 is placed in the axial direction and has an upper end connected to the respective position-limiting protrusion boss 401 and plays a role of position limiting and guidance of the second inner circular vertical bar 306 and the first location vertical bar 307 of the safety protection sleeve 3. Between the two adjacent outer guidance flanges 405 is provided protrusion flange 406 along the circumference which interference fits the protrusion point 308 on the first location vertical bar 307 of the safety protection sleeve 3 so that any upward movement of the safety protection sleeve 3 actuated not by man is limited. The pressure seat is provided on the middle part of the inner wall thereof with at least two fastening protrusions 407 uniformly distributed along the circumference and on the lower part of the inner wall thereof with at least two inner guidance flanges 408 uniformly distributed along the circumference and oriented in the axial direction. A guidance groove 409 is formed between two adjacent inner guidance flanges 408.

Figure 10:
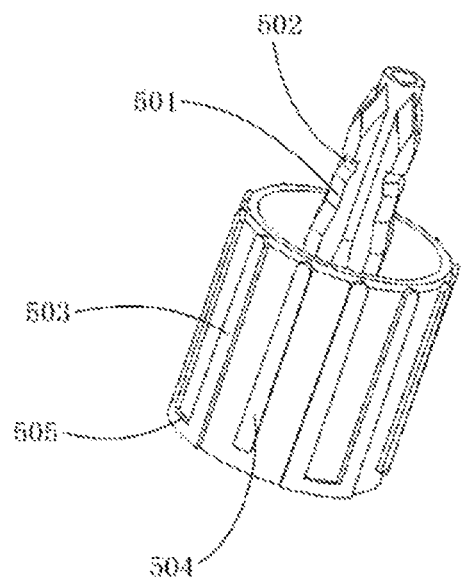
FIG. 10 is a structural schematic view of the pressure seat of the present invention.
Figure 11:
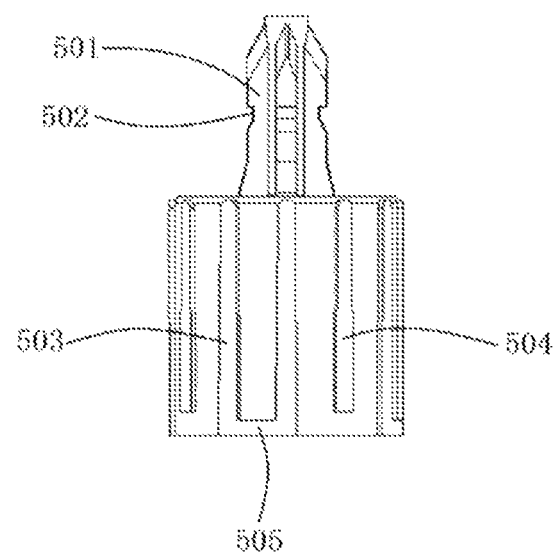
FIG. 11 is a front view of the needle holder of the present invention.
Figure 12:
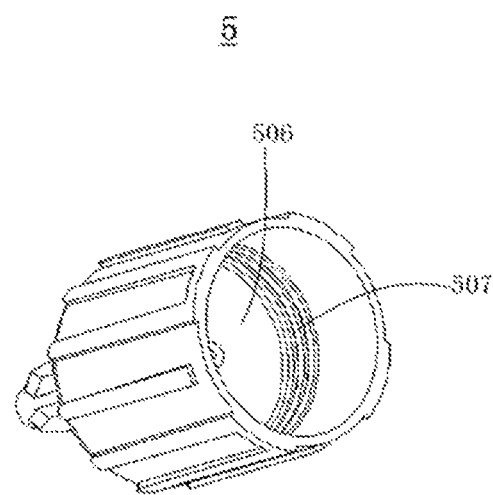
FIG. 12 is another structural schematic view of the needle holder of the present invention.

As illustrated in FIGS. 10 through 12, the needle holder has an upper part used as an installation base installing the needle, in the cylindrical form, provided on the outer wall thereof with at least two guidance fastening flanges 501 uniformly distributed along the circumference and in the axial direction, having an upper end in the form of the triangular head, cooperates with the inner guidance flange 408 and guidance groove 409 of the pressure seat to prevent the needle holder 5 and the pressure seat from rotation in relation to each other. The guidance fastening flange 501 is provided thereon with a clutch opening 502 which cooperates with the fastening protrusion 407 of the pressure seat so as to prevent the needle holder 5 and the pressure seat from axial movement in relation to each other. The needle holder 5 has a lower part used as the installation base for installing the insulin pen, in the form of cylinder and whose upper end surface cooperates with the second location step 302 of the safety protection sleeve 3 in a manner of axial position limiting.

The needle holder is provided on the outer wall of the lower part with at least two position-limiting vertical bars 503 uniformly distributed along the circumference and with at least one position-limiting bar 504. The position-limiting vertical bars 503 and position-limiting bar 504 each are oriented in the axial direction. Between the lower ends of the two adjacent position-limiting vertical bars 503 is provided a position-limiting platform 505 in the circumference.

The position-limiting vertical bar 503 and the position-limiting bar 504 cooperate with the third inner circular vertical bar 312 and the second location vertical bar 313 of the safety protection sleeve 3 so as to avoid the relative rotation between the needle holder 5 and the safety protection sleeve 3. The position-limiting platform 505 cooperates with the lower end of the third inner circular vertical bar 312 of the safety protection sleeve 3 so as to avoid downward movement of the safety protection sleeve in the axial direction. The position-limiting bar 504 has a lower end being a flat surface and cooperating with the position-limiting step protrusion 314 provided on one side of the lower end of the second location vertical bar 313 of the safety protection sleeve 3. When the safety protection sleeve 3 rotates clockwise, the surface of the lower end of the position-limiting bar 504 engages with the surface of the position-limiting step protrusion 314 of the safety protection sleeve 3 and there is no relative axial movement between the needle holder and the safety protection sleeve 3; when the safety protection sleeve 3 rotates counter-clockwise, the said relative axial movement is released.

The needle holder 5 is provided on the inner cavity of the lower part thereof with a radial platform 506 of which the upper side is linked to the upper part of the needle holder 5 and which cooperates with the inner position-limiting protrusion boss 310 of the safety protection sleeve 3 and the lower end surface of the pressure seat in a manner of axial position limiting. The needle holder 5 is provided on the inner wall of the lower part thereof with a portion corresponding to the lower side of the radial platform 506 and with internal thread 507.

Figure 13:
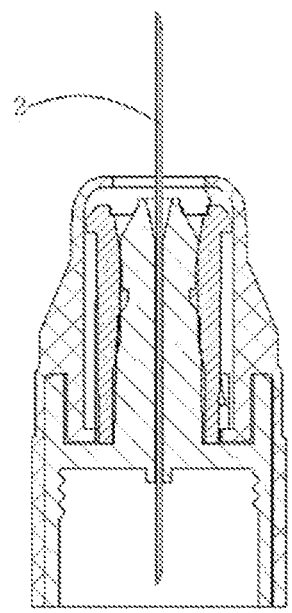
FIG. 13 is an installment position of the needle of the present invention.

As illustrated in FIG. 13, the needle 2 is fixed on the upper part of the needle holder 5 and has an upper end upward penetrating the top end of the needle holder 5 and through the needle penetration hole 301 of the safety protection sleeve 3. The needle 2 also has a lower end downward penetrating the radial platform 506 and extending into the inner cavity of the lower part of the needle holder 5.

Figure 14:
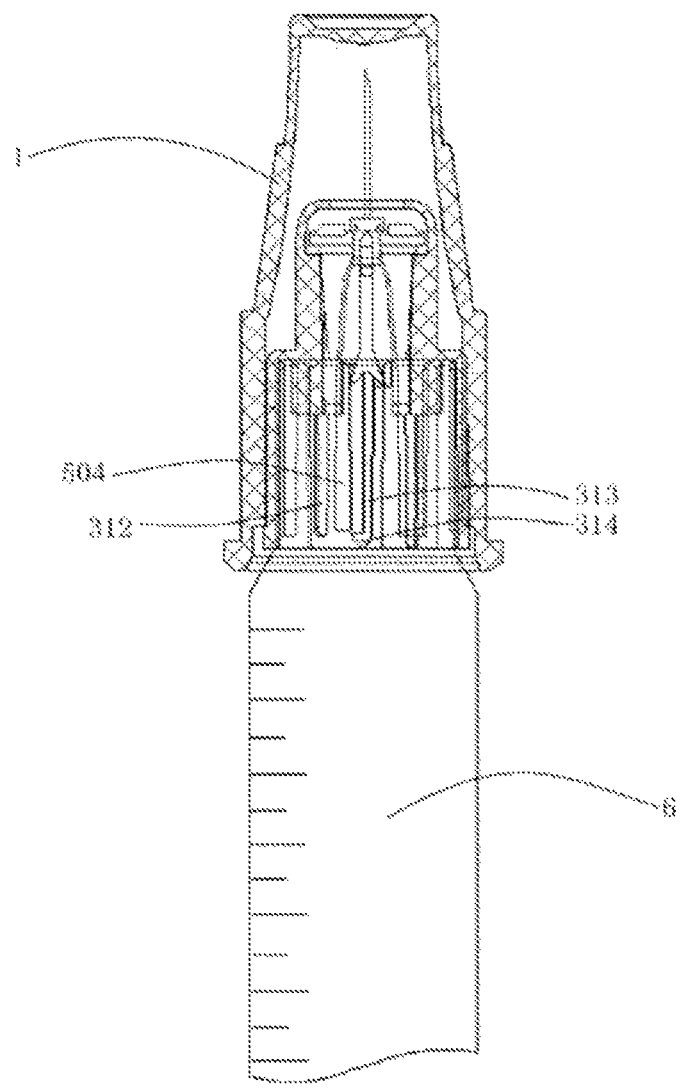
FIG. 14 is a structural schematic view of the installment structure of the present invention and an insulin pen.
Figure 15:
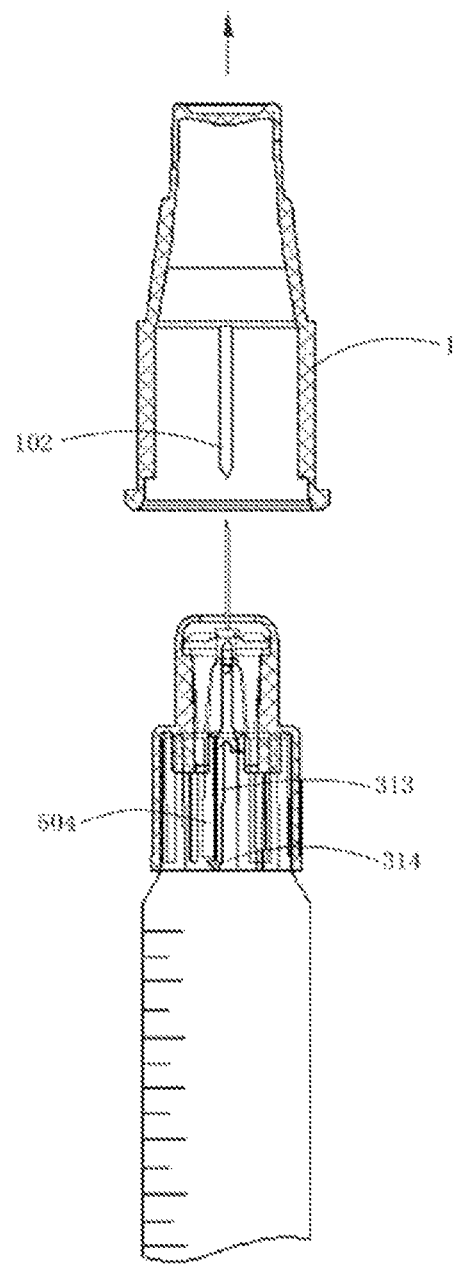
FIG. 15 is a schematic view of the state of usage of the present invention and the insulin pen.
Figure 16:
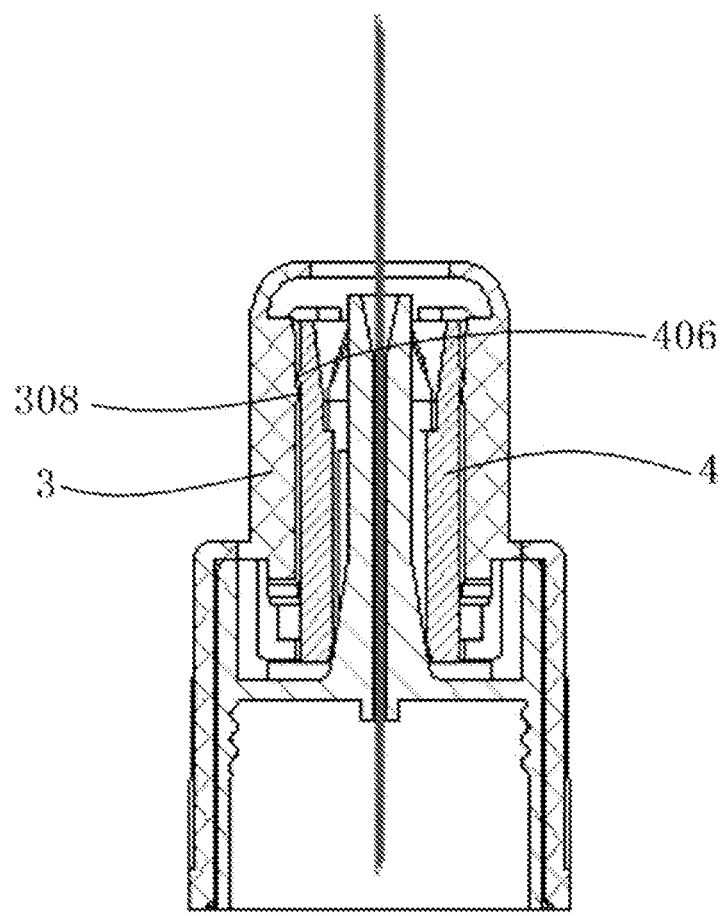
FIG. 16 is a schematic view of the state of usage of the present invention without the protection sheath.

As illustrated in FIG. 14, before administration of the insulin, it is required that the safe insulin needle assembly is installed into the insulin pen 6. During the safe insulin needle assembly screws clockwise into the end part of the insulin pen 6, the protection sheath 1 will bring the safety protection sleeve 3 into synchronized rotation. As illustrated in FIG. 5, the position-limiting step protrusion 314 on one side on the lower end of the second location vertical bar 313 of the safety protection sleeve 3 has surface engaging with the surface of the lower end of the position-limiting bar 504 of the needle holder 5 so that the safety protection sleeve 3 is pulled out when the protection sheath 1 is pulled out, the end of the insulin pen 6 is installed into the cavity of the lower part of the needle holder by screw. As illustrated in FIG. 6, the protrusion point 308 on the first location vertical bar 307 of the safety protection sleeve 3 interference fits the protrusion flange 406 of the pressure seat, with the protrusion point 308 under the protrusion flange 406, the protrusion flange 406 blocking the protrusion point 308 so as to prevent the safety protection sleeve 3 from upward movement actuated not by man and hence realizing a dual protection.

Figure 17:
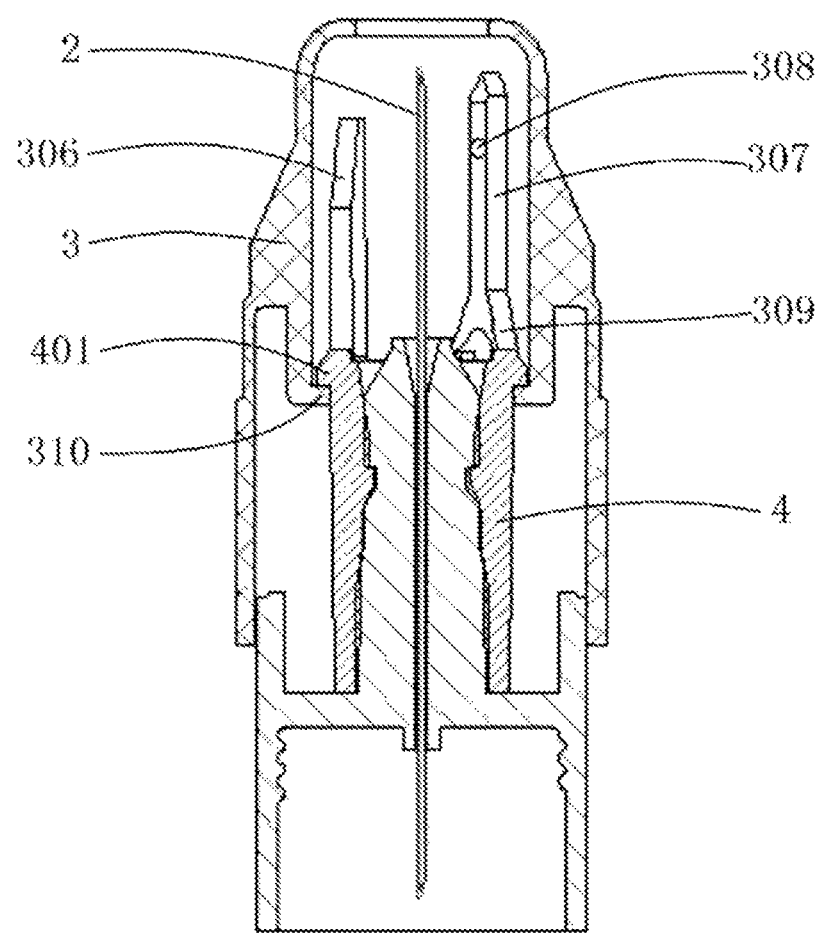
FIG. 17 is a cut view of the safety protection sleeve of the present invention under the locking state.
Figure 18:
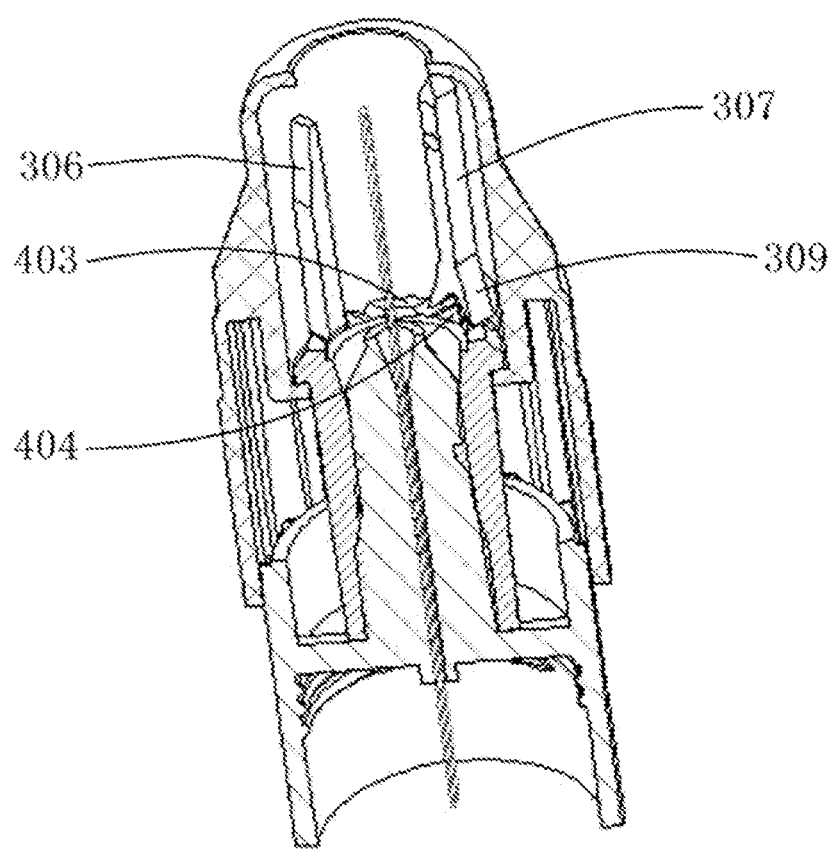
FIG. 18 is a perspective of the safety protection sleeve of the present invention under the locking state.

After administration is finished taking off the protection sheath 1, the safety protection sleeve 3 is rotated counter clock wise into place so that the position-limiting step protrusion 314 on one side of the lower end of the second location vertical bar 313 of the safety protection sleeve 3 is detached from the lower end of the position-limiting bar 504 of the needle holder 5, then the safety protection sleeve 3 is pulled upward, so that as illustrated in FIG. 17 and FIG. 18, the protrusion point 308 of the safety protection sleeve 3 goes beyond the protrusion flange 406 of the pressure seat, the inner position-limiting protrusion boss of the safety protection sleeve 3 reaches the lower part of the position-limiting protrusion boss 401 of the pressure seat 4 and abuts upward the position-limiting protrusion boss 401. Meanwhile the second inner circular vertical bar 306 of the safety protection sleeve 3 passes the respective position-limiting opening and moves upward, the position-limiting opening 402 cooperates with the second inner circular vertical bar 306 to avoid large range of oscillation of the safety protection sleeve 3 on the axial plane, the first location vertical bar 307 then moves upward till the first location vertical bar 307 is above the relevant position-limiting opening 402. The position-limiting protrusion 309 protruded to each side and on the lower end of the first location vertical bar 307 cooperates with the position-limiting bar 403, anti-reversal tooth groove 404, the position-limiting block 403 prevents the first location vertical bar 307 from rotation in the circumference, the anti-reversal tooth groove 404 prevents the first location vertical bar 307 from reversal in the axial direction, finally the safety protection sleeve 3 can't rotate in the circumference and can't move in the axial direction in order for self block. The needle 2 is completely covered by the safety protection sleeve 3 to be safely protected.

It should be indicated that the present invention after a full description can be realized by means of various change, not being limited within the best embodiments mentioned above. The above-mentioned embodiments can only be sees as description of the invention, not the limit to the invention. In conclusion the protection scope of the invention comprises those varieties, changes and substitutes being apparent to those ordinary skilled in the art.

The invention claimed is:

1. A safe insulin needle assembly comprising a protection sheath, a needle, a safety protection sleeve, a pressure seat and a needle holder, the needle is arranged on the central axis of the needle holder, the pressure seat is sheathed over the upper portion of the needle holder; the safety protection sleeve is sheathed on the needle holder and the pressure seat as a whole; the upper portion of the safety protection sleeve is connected to and cooperates with the pressure seat; the needle protrudes out of the top end of the upper portion of the safety protection sleeve; the lower portion of the safety protection sleeve is connected to and cooperates with the lower portion of the needle holder; the protection sheath is sheathed on the safety protection sleeve and the needle as a whole; and the lower portion of the protection sheath is connected to and cooperates with the lower portion of the safety protection sleeve;

the protection sheath having a hollow cavity; an upper portion in the form of a hollow truncated cone; the lower portion in the form of a cylinder, the diameter of the lower portion is larger than that of the lower edge of the upper portion of the protection sheath; a first location step in an annular form, provided at the connection between the upper portion and the lower portion of the protection sheath; a top end in a closed form on the upper portion of the protection sheath; an inner wall on the lower portion of the protection sheath, provided thereon with at least two first inner circular vertical bars uniformly distributed along the circumference, oriented in the axial direction;

the safety protection sleeve having a hollow cavity; the upper portion and the lower portion each in the form of a cylinder; a top end on the upper portion, provided thereon with a needle penetration hole, the diameter of the upper portion being smaller than that of the lower portion; a second location step, in an annular form, provided at the connection between the upper portion and the lower portion; the first location step cooperating with the second location step in the manner of axial position limiting; the outer wall on the lower portion of the safety protection sleeve provided thereon with a circular outer location protrusion boss along the lower edge of the outer wall, with at least two outer location bars uniformly distributed along the circumference, oriented in the axial direction and having a lower end which is linked to the outer location protrusion boss; a free position surface provided between the outer location bars, used for the insertion of the first inner circular vertical bar and interference fit therebetween;

an inner wall on the upper portion of the safety protection sleeve, provided thereon with at least two second inner circular vertical bars uniformly distributed along the circumference and at least one first location vertical bar, each oriented in the axial direction; the first location vertical bar provided thereon with a protrusion point, having a lower end provided thereon with a position-limiting protrusion protruded to each side; the inner wall of the upper portion of the safety protection sleeve provided thereon with a circular inner position-limiting protrusion boss along the lower edge of the inner wall; an inner wall on the lower portion of the safety protection sleeve provided thereon with at least two third inner circular vertical bars uniformly distributed along the circumference and at least one second location vertical bar, each oriented in the axial direction; a lower end on the second location vertical bar and being provided thereon with a position-limiting step protrusion deflected to one side;

the pressure seat being in a cylinder form, having an outer wall provided on the upper edge thereof with at least two position-limiting protrusion bosses uniformly distributed along the circumference, the position-limiting protrusion boss having an outer side snugly fitting the inner wall of the upper portion of the safety protection sleeve, the position-limiting protrusion boss cooperating with the inner position-limiting protrusion boss of the safety protection sleeve in a manner of axial position limiting, a position-limiting opening provided between two adjacent position-limiting protrusion bosses, used for upward penetration of the second inner circular vertical bar and first location vertical bar of the safety protection sleeve; the position-limiting protrusion bosses each having a upper surface provided thereon with a position-limiting block, the part between two adjacent position-limiting blocks constituting an anti-reversal tooth groove, the position-limiting block and the anti-reversal tooth groove cooperating with the position-limiting protrusion on the lower portion of the first location vertical bar of the safety protection sleeve; the outer wall of the pressure seat provided thereon with at least two outer guidance flanges uniformly distributed along the circumference, corresponding to the position limiting protrusion bosses respectively, oriented in the axial direction and cooperating with the second inner circular vertical bar and the first location vertical bar of the safety protection sleeve; the outer guidance flange having an upper end, between the upper ends on two adjacent outer guidance flanges being provided thereon with protrusion flange along the circumference, interference fitting the protrusion point on the first location vertical bar of the safety protection sleeve; the inner wall of the pressure seat having a middle portion which is provided thereon with at least two clutch protrusions uniformly distributed along the circumference, the inner wall of the pressure seat having a lower portion which is provided thereon with at least two inner guidance flanges uniformly distributed along the circumference, oriented in the axial direction; the needle holder having the upper portion in a tube form, an outer wall on the upper portion provided thereon with at least two guidance fastening flanges uniformly distributed along the circumference, oriented in the axial direction and cooperating with the inner guidance flange of the pressure seat, the guidance fastening flange provided thereon with a clutch opening cooperating with the clutch protrusion of the pressure seat;

the needle holder having the lower portion in a cylindrical form, the lower portion having an upper end face cooperating with the second location step of the safety protection sleeve in a manner of axial position limiting, the lower portion of the needle holder having an outer wall provided thereon with at least two position-limiting vertical bars and at least one position-limiting bar uniformly distributed along the circumference, each oriented in the axial direction and cooperating with the third inner circular vertical bar and second location vertical bar of the safety protection sleeve, the position-limiting bar having a lower end cooperating with the position-limiting step protrusion on one side of the lower end of the second location vertical bar of the safety protection sleeve; the lower portion on the needle holder having an inner cavity which is provided thereon with a radial platform having an upper side linked to the upper portion of the needle holder, the radial platform cooperating with the inner position-limiting protrusion boss of the safety protection sleeve and the lower end face of the pressure seat in a manner of axial position limiting, the inner wall on the lower portion of the needle holder having a part corresponding to the lower portion of the radial platform, which is provided with internal thread.

2. The safe insulin needle assembly according to claim 1, wherein at least one of the lower end on the first inner circular vertical bar of the protection sheath, the top end on the outer location bar of the safety protection sleeve, the top end on the first location vertical bar of the safety protection sleeve and the top end on the guidance fastening flange is shaped as a triangular head.

3. The safe insulin needle assembly according to claim 2, wherein the inner position-limiting protrusion boss is linked to the lower end of the second inner circular vertical bar, and is provided on the part corresponding to the lower end of the first location vertical bar with a gap.

4. The safe insulin needle assembly according to claim 1, wherein the upper end on the outer guidance flange of the pressure seat is linked to the corresponding position-limiting protrusion boss.

5. The safe insulin needle assembly according to claim 4, wherein the lower ends of the two adjacent position-limiting vertical bars of the needle holder is provided therebetween with position-limiting platform along the circumference, cooperating with the lower end on the third inner circular vertical bar of the safety protection sleeve so that the axial downward movement of the safety protection sleeve is prevented.

6. The safe insulin needle assembly according to claim 1, wherein the lower end of the position-limiting bar is flat in such a manner that the lower end cooperates with the plane on the position-limiting step protrusion on one side of the lower end on the second location vertical bar of the safety protection sleeve.

7. The safe insulin needle assembly according to claim 1, wherein the needle is secured on the upper portion of the needle holder with the upper end upward penetrating out of the top end on the upper portion of the needle holder and out of the needle penetration hole of the safety protection sleeve, the lower end of the needle downward penetrating through the radial platform and extending into the inner cavity of the lower portion of the needle holder.

\* \* \* \* \*